United States Patent [19]
Prescott

[11] Patent Number: 6,082,997
[45] Date of Patent: Jul. 4, 2000

[54] DENTAL PROPHYLAXIS PASTE HOLDER

[76] Inventor: Phyllis Matuska Prescott, 7951 W. Charleston, #134, Las Vegas, Nev. 89117

[21] Appl. No.: 09/209,965

[22] Filed: Dec. 10, 1998

Related U.S. Application Data

[60] Provisional application No. 60/073,845, Jan. 12, 1998.

[51] Int. Cl.[7] ........................................................ A61C 1/14
[52] U.S. Cl. .............................. 433/49; 433/163; 224/217
[58] Field of Search .................... 433/49, 163; 206/63.5; 224/217

[56] References Cited

U.S. PATENT DOCUMENTS

| | | | |
|---|---|---|---|
| 1,545,452 | 7/1925 | Pinn | 433/163 |
| 2,222,741 | 11/1940 | Bush | 433/163 |
| 4,717,057 | 1/1988 | Porteous | 433/49 |
| 5,048,731 | 9/1991 | Moreschini | 433/163 |
| 5,249,963 | 10/1993 | McGarrigle | 433/163 |
| 5,732,862 | 3/1998 | Bull | 433/163 |

*Primary Examiner*—John J. Wilson
*Attorney, Agent, or Firm*—Quirk & Tratos

[57] ABSTRACT

A device for securing dental prophylaxis paste to the hand of a dental professional performing a dental cleaning. The device includes a receptacle with an opening at the top and a closed bottom. The receptacle is sized to receive a standard sized cup of pre-packaged dental prophylaxis paste. A deformable loop is connected to the receptacle for securing the receptacle to the finger of a dental professional. A support leg protrudes from the receptacle to bear against a finger adjacent to the encircled finger to thereby prevent the dental prophylaxis paste holder from rotating around the dental professional's finger.

9 Claims, 2 Drawing Sheets

DENTAL PROPHYLAXIS PASTE HOLDER

RELATED APPLICATION DATA

This application claims the benefit of U.S. Provisional Patent Application Ser. No. 60/073,845 filed Jan. 12, 1998.

FIELD OF THE INVENTION

The present invention relates to holders for dental prophylaxis paste. In particular, the present invention is a device for securing standard sized, pre-packaged cups of dental prophylaxis paste to a dental professional's hand.

BACKGROUND OF THE INVENTION

Dentists recommend that patients regularly receive professional tooth cleaning to prevent tooth decay and cavities. In a typical professional cleaning, the dental professional uses a dental angle with a rotating applicator tip to apply dental prophylaxis paste to the patient's teeth and scrub any accumulated plaque and tartar off the teeth. To insure that the cleaning is thorough, the dental professional frequently adds dental prophylaxis paste to the applicator tip from a small, pre-packaged, disposable cup of standard size and shape. These cups, however, can be difficult to handle. Because the dental professional has the dental angle in one hand and is manipulating the patient's mouth or holding an instrument with the other hand, it is often difficult and inconvenient to stabilize the cup while cleaning a patient's teeth.

There are several devices available which attempt to remedy this problem. For example, one device is shaped like a ring, with a band to encircle a finger integral with a collar to hold a cup of dental prophylaxis paste adjacent to the dental professional's finger. The disadvantage of this device is that it lacks a structure to prevent articulation of the device. Thus, the device does not provide the stability desired because the device tends to rotate around the dental professional's finger when the applicator tip is pressed into the cup.

Another device for holding dental prophylaxis paste has an S-shaped handle depending from the lip of a well. The device is held such that the handle curls over the index finger and is secured from rotation by contacting the thumb at the second curl. Alternatively, the device could be held with the handle curling around the inside of one finger with the second curl bearing against the outside of an adjacent finger. The well is filled with dental prophylaxis paste.

If the device is secured with the thumb, one disadvantage of the device is that the hand could become fatigued from gripping the device for the duration of the dental cleaning procedure. Yet another disadvantage of this device is that the well must be filled with dental prophylaxis paste because the well is not adapted to receive pre-packaged cups of dental prophylaxis paste.

If the device is secured by an adjacent finger, one disadvantage of this device is that while the S-shaped handle helps to prevent articulation of the device around the fingers, the curl of the handle bearing against the dental professional's finger urges the well backwards toward the dental professional's hand. The awkward position of the well forces the dental professional to turn his or her hand to access the well containing the dental prophylaxis paste. Also, the backward tilt of the well may allow dental prophylaxis paste to fall from the well during normal use.

Regardless of how the device is held, a further disadvantage of this device is that, due to the S-shape of the handle, the dental professional must use two fingers, or a finger and the thumb, on the handle to secure the device. In other words, the device is not secured to a single finger but requires the cooperation of two fingers, or a finger and the thumb, to hold the device to the hand. This can interfere with a dental professional's ability to perform the cleaning procedure because the hand holding the device is unable to hold other instruments or manipulate the patient's mouth.

Thus, it can be seen that there is a need for a device which holds a standard size cup of dental prophylaxis paste in a stable position without interfering with the dental professional's ability to perform the dental cleaning procedure.

SUMMARY OF THE INVENTION

The present invention is a device for holding dental prophylaxis paste. A receptacle is provided which is sized to hold a standard size cup of dental prophylaxis paste. The receptacle has an open top, a closed bottom, and may be cylindrical, conical, or frusto-conical. A loop is attached to the receptacle. The loop may be formed from a deformable material, such as plastic, to accommodate different size fingers. A support leg depends from the receptacle. The support leg extends past the bottom of the receptacle in a direction substantially perpendicular to the receptacle opening. In a preferred embodiment, the receptacle, handle, and support leg are integrally formed.

In use, the loop encircles a finger of a dental professional to secure the receptacle to the dental professional's hand. The device may be secured to a finger with the receptacle on the inside of the hand or on the outside of the hand leaving the fingers free to grasp instruments or manipulate the patient's mouth. The support leg bears against one or more fingers adjacent to the encircled finger. By bearing against the dental professional's fingers, the support leg prevents articulation of the receptacle, especially rotation about the dental professional's finger.

It is an object of the present invention to provide a device which can hold dental prophylaxis paste in a stable fashion. Another object of the present invention is to provide a device which can receive a standard size cup of dental prophylaxis paste. Yet another object is to provide a device which secures a cup of dental prophylaxis paste to the dental professional's hand and orients and positions the cup so that neither the device nor the cup of dental prophylaxis paste interferes with the dental professional's ability to perform the cleaning procedure. Another object of the invention is to provide a dental prophylaxis paste holder which can accommodate a range of finger sizes.

DESCRIPTION

Figure 1:
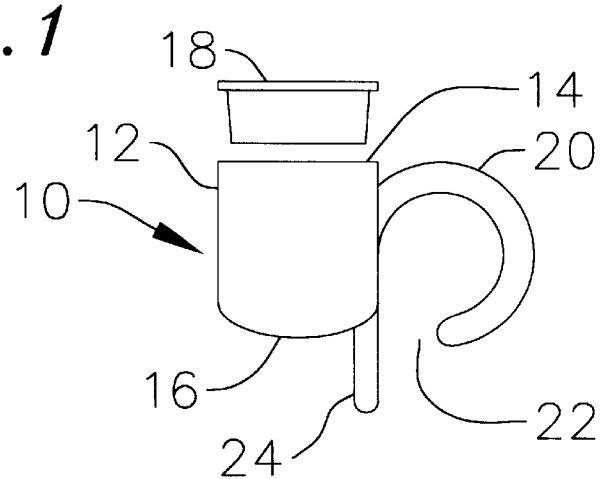
FIG. 1 is a left side view of an embodiment of the present invention.
Figure 2:
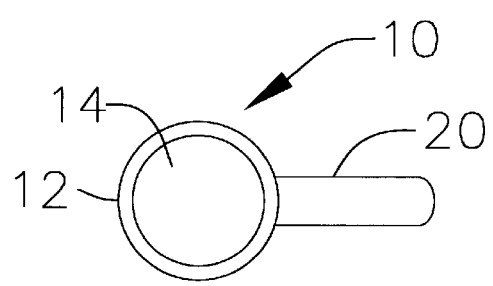
FIG. 2 is a top view of the embodiment of FIG. 1
Figure 3:
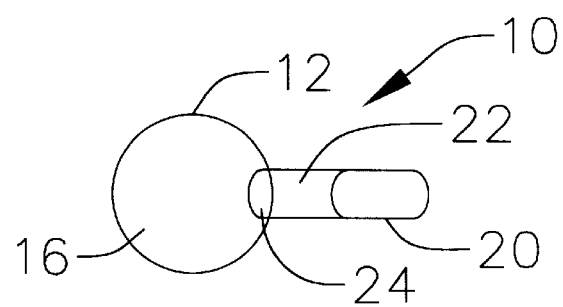
FIG. 3 is a bottom view of the embodiment of FIG. 1.
Figure 4:
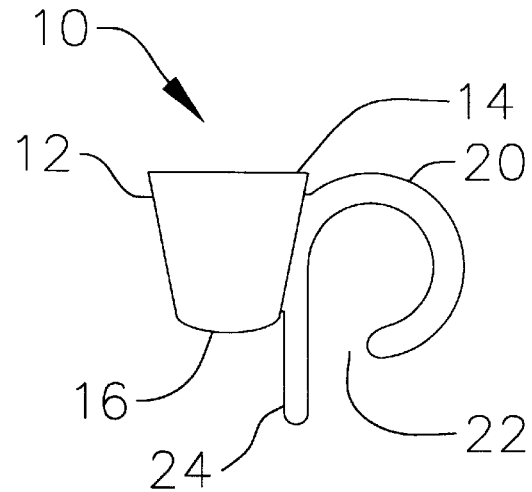
FIG. 4 is a left side view of an alternate embodiment of the present invention.

Reference is now made to the figures wherein like parts are referred to by like numerals throughout. Referring to FIGS. 1–3, the dental prophylaxis paste holder 10 includes a receptacle 12. The receptacle 12 could be cylindrical, conical, or frusto-conical in shape. For example, the dental prophylaxis paste holder 10 of FIG. 4 is substantially frusto-conical. Referring again to FIGS. 1–3, the receptacle 12 has an opening 14 at the top and a closed bottom 16. Thus, dental prophylaxis paste could be placed directly into the receptacle 12. However, in the preferred embodiment, the receptacle 12 has a size and shape adapted to receive a standard sized, pre-packaged, disposable cup 18 of dental prophylaxis paste 18. The cup 18, known in the art, is substantially frusto-conical with a flat lip around its rim. The cup 18 is inserted into the receptacle opening 14 and is held in place by friction.

A loop 20 for securing the receptacle 12 to a dental professional's finger is attached to the exterior wall of the receptacle 12. While it is contemplated that the loop 20 could completely encircle the dental professional's finger, in a preferred embodiment, the loop 20 includes a gap 22. Also, the loop 20 is preferably formed from a deformable material such as plastic or metal. The gap 22, coupled with the deformable material comprising the loop 20, allows the loop 20 to deform to accommodate a range of finger sizes.

Depending from the receptacle 12 is a support leg 24 aligned with the loop 20. As shown in FIGS. 1 and 4, the support leg 24 extends past the receptacle bottom 16 in a direction substantially perpendicular to the receptacle opening 14 regardless of the shape of the receptacle 12. The support leg 24 is of a length to bear against one or more fingers adjacent to the finger encircled by the loop 20. In a preferred embodiment, the support leg 24 only bears against the next adjacent finger.

The receptacle 12, loop 20, and support leg 24 could be attached to one another using fasteners, adhesives, bonding, or the like. However, in a preferred embodiment, the receptacle 12, loop 20, and support leg 24 are integrally molded from a plastic. The plastic preferably has characteristics, such as a high melting point, which allow the dental prophylaxis device 10 to be sterilized in an autoclave.

Figure 5:
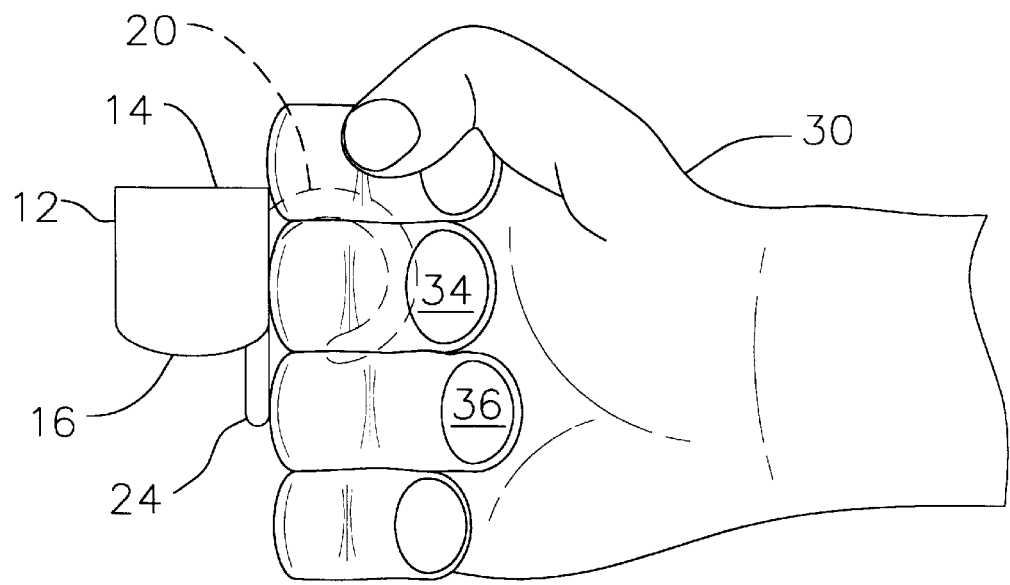
FIG. 5 is a left side view of the embodiment of FIG. 1 on the outside of a dental professional's hand.
Figure 6:
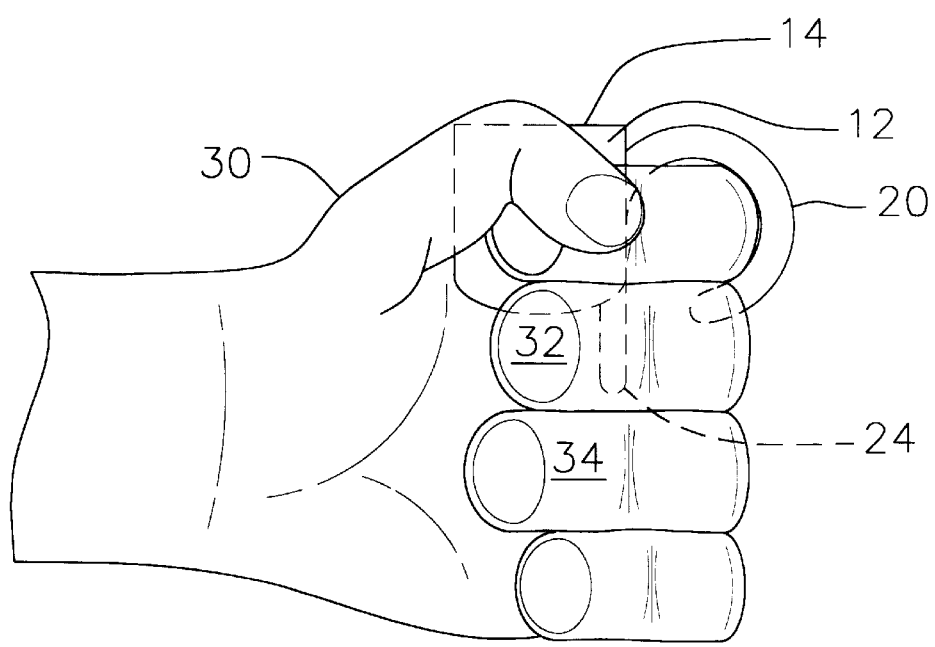
FIG. 6 is an elevated view of the embodiment of FIG. 1 on the inside of a dental professional's hand.

In use, a standard cup 18 of dental prophylaxis paste is inserted into the dental prophylaxis paste holder 10 and the dental prophylaxis paste holder 10 is secured to the dental professional's hand 30. FIGS. 5 and 6 illustrate how the dental prophylaxis paste holder 10 may be held. Referring first to FIG. 5, the loop 20 could be secured to any finger with the receptacle 12 on the back of the finger. For example, in FIG. 5, the loop 20 surrounds the middle finger 34. The support leg 24 bears against the ring finger 36. Thus, when a force is imparted to the receptacle 12, or the cup 18 retained therein, the support leg 24 prevents the receptacle 12 from articulating around the middle finger 34.

Alternatively, the dental prophylaxis paste holder 10 could be secured to the inside of the hand 30. For example, in FIG. 6 the loop 20 surrounds the index finger 32 with the receptacle 12 on the inside of the hand 30. The fingers may be curled around the receptacle 12. However, it is not necessary to curl the fingers around the receptacle 12 because the support leg 24 bears against the inside of the middle finger 34 to thereby prevent the receptacle 12 from rotating when a force is imparted to the receptacle 12 or the cup 18 in the receptacle 12.

During the dental cleaning procedure, the dental professional holds the dental angle in the dominant hand (i.e. in the right hand for a right-handed person or the left hand for a left-handed person). The dental prophylaxis paste holder 10 is secured to the other hand 30 with the loop 20. Because the dental prophylaxis paste holder 10 is secured to the dental professional's hand, the dental professional is free to use the fingers on that hand to manipulate the patient's mouth or hold instruments. Similarly, the dental professional's hand 30 is less likely to suffer fatigue because the dental prophylaxis holder 10 is secured to a finger rather than gripped in the hand or pinched between two fingers.

The dental professional charges the dental angle with a quantity of dental prophylaxis paste by pressing the applicator tip into the cup 18 and scooping an amount of dental prophylaxis paste onto the applicator tip. As the cleaning procedure proceeds, the dental professional adds dental prophylaxis paste to the applicator tip in a similar fashion as necessary.

An advantage of the present invention is that the dental prophylaxis paste is held in a stable fashion against the dental professional's hand 30. Specifically, the support leg 24 prevents the dental prophylaxis paste holder 10 from rotating around the dental professional's finger. Yet another advantage of the present invention is that the loop 20 can accommodate a range of finger sizes. A further advantage of the present invention is that the receptacle 12 is sized to receive a standard sized pre-packaged cup 18 of dental prophylaxis paste. Another advantage of the present invention is that the dental prophylaxis paste holder 10 is positioned so that the dental professional does not have to repeatedly rotate the hand 30 to access the cup 18 containing dental prophylaxis paste. Likewise, because the dental prophylaxis paste holder 10 is secured to the dental professional's hand 30, the fingers of that hand are free to hold other instruments or manipulate the patient's mouth.

What is claimed is:

1. A hand held device for holding dental prophylaxis paste comprising:
    a receptacle to hold the paste, said receptacle having an opening and a bottom;
    a support leg depending from a position at the side a distance from the bottom of the receptacle in a direction orthogonal to the opening; and
    a loop attached to the side proximate said position and extending from said side and adapted to be disposed about a finger to locate the receptacle in either of a palmar inside or outside position, said leg adapted to rest against the fingers to resist articulation of the receptacle.

2. The device of claim 1 wherein said loop is plastically deformable to fit different sized fingers.

3. The device of claim 1 wherein said receptacle is cylindrical.

4. The device of claim 3 wherein said leg extends in a direction substantially parallel to the axis or the receptacle.

5. The device of claim 1 wherein the receptacle is conical.

6. The device of claim 5 wherein said leg extends in a direction substantially parallel to the axis of the receptacle.

7. The device of claim 1 wherein said loop is attached to said leg.

8. A hand held device for holding a cup of dental prophylaxis paste comprising:
    a receptacle to hold the cup, said receptacle being one of cylindrical or conical and having an opening to receive the cup, a bottom and an axis;
    a support leg depending from a position at the side a distance from the bottom of the receptacle in a direction substantially parallel to said axis; and
    a loop attached to the side proximate said position and projecting from said side and adapted to be disposed about a finger to locate the receptacle in either of a palmar inside or outside position, said leg adapted to rest against the fingers to resist articulation of the receptacle.

9. A hand held device for holding dental prophylaxis paste comprising:
- a receptacle to hold the paste, said receptacle being cylindrical or conical and having one an opening, a bottom and an axis;
- a support leg depending from a position at the side a distance from the bottom of the receptacle in a direction substantially parallel to said axis; and
- a deformable loop attached to the side proximate said position and extending from said side and adapted to be disposed about a finger to locate the receptacle in either of a palmar inside or outside position, said leg adapted to rest against the fingers to resist articulation of the receptacle.

* * * * *